(12) United States Patent
Warburton-Pitt et al.

(10) Patent No.: US 7,093,859 B2
(45) Date of Patent: Aug. 22, 2006

(54) TUBING AND CONNECTOR ASSEMBLY

(75) Inventors: Stephen Ronald Warburton-Pitt, Queensbury, NY (US); Rick Alan Steele, Newton, NJ (US)

(73) Assignee: Saint-Gobain Performance Plastics Corporation, Wayne, NJ (US)

(*) Notice: Subject to any disclaimer, the term of this patent is extended or adjusted under 35 U.S.C. 154(b) by 205 days.

(21) Appl. No.: 10/785,549

(22) Filed: Feb. 24, 2004

(65) Prior Publication Data

US 2004/0164555 A1 Aug. 26, 2004

Related U.S. Application Data

(60) Continuation of application No. 09/951,366, filed on Sep. 13, 2001, now abandoned, which is a division of application No. 08/909,450, filed on Aug. 11, 1997, now Pat. No. 6,290,265.

(51) Int. Cl.
*F16L 47/02* (2006.01)

(52) U.S. Cl. ............... 285/131.1; 285/285.1; 285/293.1; 285/423; 604/284

(58) Field of Classification Search ...... 285/FOR. 138, 285/133.11, 285.1, 293.1, 131.1, 423; 604/284; 128/214 R
See application file for complete search history.

(56) References Cited

U.S. PATENT DOCUMENTS

| | | | |
|---|---|---|---|
| 3,458,619 A | 7/1969 | Prochaska | |
| 3,463,691 A | 8/1969 | Martin | |
| 3,540,223 A | 11/1970 | Ebbe | |
| 4,070,044 A | 1/1978 | Carrow | |
| 4,076,282 A | 2/1978 | Scott, Jr. et al. | |
| 4,203,436 A | 5/1980 | Grimsrud | |
| 4,596,557 A | 6/1986 | Pexa | |
| 4,661,110 A | 4/1987 | Fortier et al. | |
| 4,795,465 A | 1/1989 | Marten | |
| 4,815,769 A | 3/1989 | Hopperdietzel | |
| 4,997,213 A | 3/1991 | Traner et al. | |
| 5,254,097 A | 10/1993 | Schock et al. | |
| 5,292,305 A | 3/1994 | Boudewijn et al. | |
| 5,411,300 A | 5/1995 | Mitsui | |
| 5,429,397 A | 7/1995 | Kanao | |
| 5,447,341 A | 9/1995 | Hartel et al. | |
| 5,453,088 A | 9/1995 | Boudewijn et al. | |
| 5,568,949 A | 10/1996 | Andre | |
| 5,945,052 A | 8/1999 | Schryver et al. | |
| 6,432,345 B1 | 8/2002 | Warburton-Pitt | |

FOREIGN PATENT DOCUMENTS

| | | |
|---|---|---|
| CA | 580160 | 7/1959 |
| JP | 6-42687 | 2/1994 |
| JP | 6-101791 | 4/1994 |
| JP | 40-6101792 | 4/1994 |

OTHER PUBLICATIONS

Sani-Tech, Inc., "Creating a World Standard in Sanitary Connective Technology", Catalog, Copyright 1991, pp. 1-10.

*Primary Examiner*—James M. Hewitt
(74) *Attorney, Agent, or Firm*—Larson Newman Abel Polansky & White, LLP; Chi Suk Kim

(57) ABSTRACT

A connector and tubing assembly including a multi-lumen molded connector having at least three flexible tubes also molded into the connector. The connector may be "Y" shaped and include three flexible tubes. A process of making the connector and tubing assembly involves forming a first part of the connector with two tubes molded therein and then removing an internal mold member prior to molding the final connector portion and third tube in place.

18 Claims, 3 Drawing Sheets

TUBING AND CONNECTOR ASSEMBLY

This application is a continuation of application Ser. No. 09/951,366 (now abandoned), filed on Sep. 13, 2001 which is a divisional of application Ser. No. 08/909,450 filed Aug. 11, 1997 (now U.S. Pat. No. 6,290,265), the disclosures of which are fully incorporated herein by reference.

FIELD OF THE INVENTION

The present invention generally relates to tubing and connector assemblies and, specifically, to those assemblies utilizing multi-lumen connectors.

BACKGROUND OF THE INVENTION

Tubing assemblies including flexible tubing and multi-lumen connectors have been used in many applications, including those that require a high degree of assurance that contamination will not enter the system by way of the connector. Applications of such systems include closed systems in the medical field in which the flexible tubing may be clipped into a peristaltic pump used for medical purposes. Past tubing and connector assemblies have required various means for securing the connectors to the flexible tubing, including mechanical connectors or adhesive. These systems are therefore susceptible to contaminants entering the system at the point of connection.

Connectors have been molded directly to two tubes, however, to Applicant's knowledge, there has never been an acceptable method of directly molding a multi-lumen connector to three or more flexible tubes. In general, this is due to the problems associated with maintaining fluid passages within the connector and between the multiple tubes during and after the molding process.

Therefore, it would be desirable to provide a tubing and connector assembly as well as a method of molding such an assembly in a cost-efficient manner to produce an integral tubing and connector assembly that maintains a high degree of system integrity.

SUMMARY OF THE INVENTION

The present invention therefore generally provides an integral connector and tubing assembly including a one-piece, multi-lumen connector having at least three connector portions and at least three tubes. Each of the tubes is molded into one connector portion, and a fluid path extends within each connector portion and communicates between each of the three tubes. The connector may be "Y" shaped with three connector portions respectively receiving three flexible tubes. The connector assembly may also have additional connector portions and a like number of additional flexible tubes. The connector is preferably molded from liquid silicone while the tubes are preferably flexible and formed from a thermoset silicone.

A method of molding a connector and tubing assembly of the present invention generally includes molding first and second portions of a connector around respective ends of first and second tubes while maintaining fluid passages through the first and second portions and in communication with internal fluid bores of the first and second tubes and then molding a third portion of the connector around an end of a third tube and connected with the first and second portions while maintaining a fluid passage between the end of the third tube and the fluid passages in the first and second portions. Preferably, first and second rod members are placed in the respective ends of the first and second tubes prior to molding the first and second portions and a third rod member is placed in the end of the third tube prior to molding the third portion. Prior to molding the third portion, the first and second rod members are removed from the first and second portions of the connector. The first and second rod members may be part of a "Y" shaped member and each molding step may be performed in a single mold.

A more specific and preferred method of making the connector and tubing assembly according to this invention includes the steps of: connecting the internal fluid bores of respective ends of first and second tubes to first and second rod members; placing the rod members and the ends of the first and second tubes into a first mold cavity; filling the first mold cavity with curable material to form first and second connector portions around the ends of the first and second tubes and the first and second rod members such that the first and second rod members form fluid passages through the connector; withdrawing the first and second rod members; inserting a third rod member into the internal fluid bore in an end of a third tube; placing the end of the third tube into a second mold cavity and in engagement with at least one of the fluid passages; filling the second mold cavity with additional curable material to form a third connector portion; and removing the third rod member.

Preferably, the first and second mold cavities communicate with one another in the same mold. The mold may be an injection mold. For allowing the use of a single mold, a mold insert may be placed within the second mold cavity prior to filling the first mold cavity with the curable material. This prevents the curable material from filling the second mold cavity during this initial molding step. The mold insert is generally solid but preferably includes a central hole. The first and second rod members may be part of a "Y" shaped member. In this case, the second step further includes placing a third leg of the "Y" shaped member within the central hole of the insert and placing the insert within the second mold cavity. The mold insert may have a protrusion surrounding the hole and this protrusion may then form a recess in communication with the passages in the initially formed connector portions. This recess can be used to locate or receive the third tube prior to the second molding step, i.e., prior to filling the second mold cavity with additional curable material.

Various objects and advantages of the invention will become more readily apparent to those of ordinary skill upon review of the following detailed description of one preferred embodiment taken in conjunction with the accompanying drawings.

DETAILED DESCRIPTION OF THE PREFERRED EMBODIMENT

Figure 1:
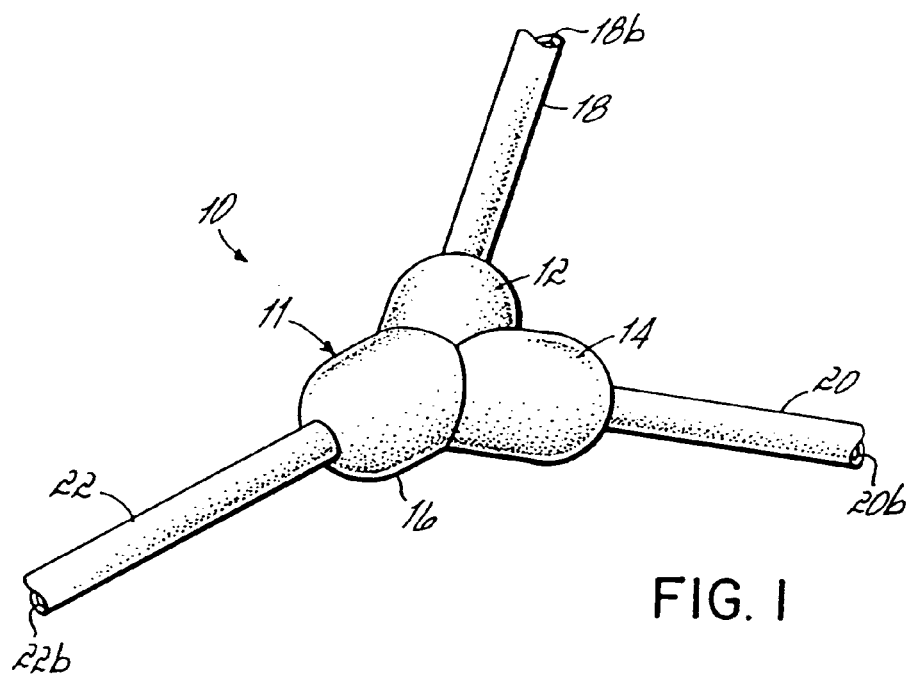
FIG. 1 is a perspective view of a connector and tubing assembly constructed in accordance with the preferred embodiment of this invention.

FIG. 1 illustrates a connector and tubing assembly 10 after a connector 11 has been molded with portions 12, 14, 16 holding flexible tubes 18, 20, 22 together for fluid communication therebetween. This structure therefore forms an integral fluid conveyance system which is not easily compromised at the junctions between connector 11 and tubes 18, 20, 22.

FIGS. 2–6 illustrate the preferred manner of making the connector and tubing assembly 10. First, a mold half 30 is provided having an internal mold cavity 31 in the shape of the desired connector 11. Cavity 31 is preferably formed by three smaller cavities 32, 34, 36 each having respective ports 38, 40, 42. Curable mold material, such as conventional liquid silicone, may be injected through ports 38, 40, 42 into cavity 31 after a second mold half is brought into facing engagement, as will be described below. Recesses 44, 46, 48 are respectively provided for holding tubes 18, 20, 22 such that respective connecting ends 18a, 20a, 22a extend within cavity portions 32, 34, 36. An inner mold member 50 is provided and may be formed from low density polyethylene (LDPE). Mold member 50 may be generally "Y" shaped and serves to help form a fluid passageway between the internal fluid bores 18b, 20b, 22b of tubes 18, 20, 22 after molding is complete.

Figure 2:
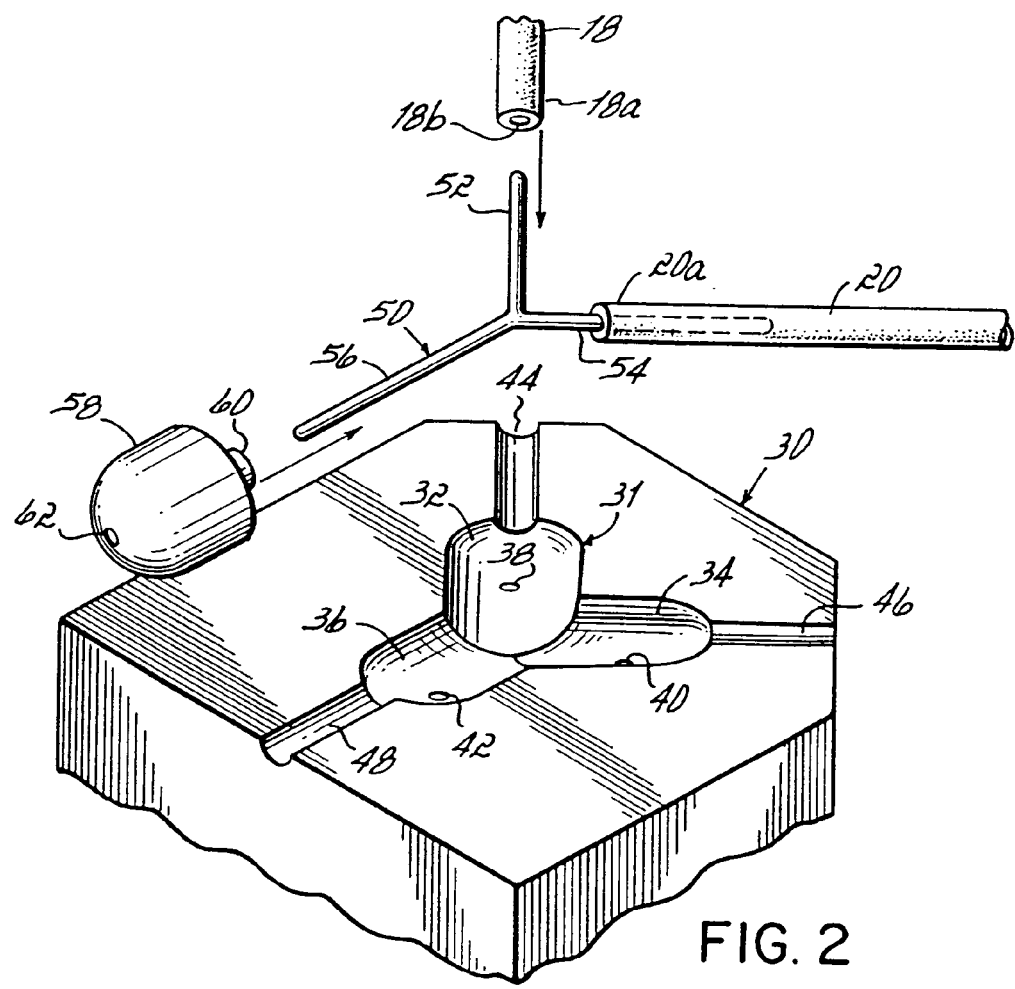
FIG. 2 is a perspective view, partially exploded, of the initial steps of a molding process used to form the product of FIG. 1.

Referring to FIG. 2, first and second tubes 18, 20 are inserted onto respective first and second rod members 52, 54 of mold member 50 and a third rod member or leg 56 receives a mold insert 58 which may be formed of metal, such as stainless steel, and generally takes the shape of cavity portion 36. Mold insert 58 includes a central protrusion on an end facing cavity portions 32, 34 and includes a central hole 62 for receiving rod member 56 of inner mold member 50.

Figure 3:
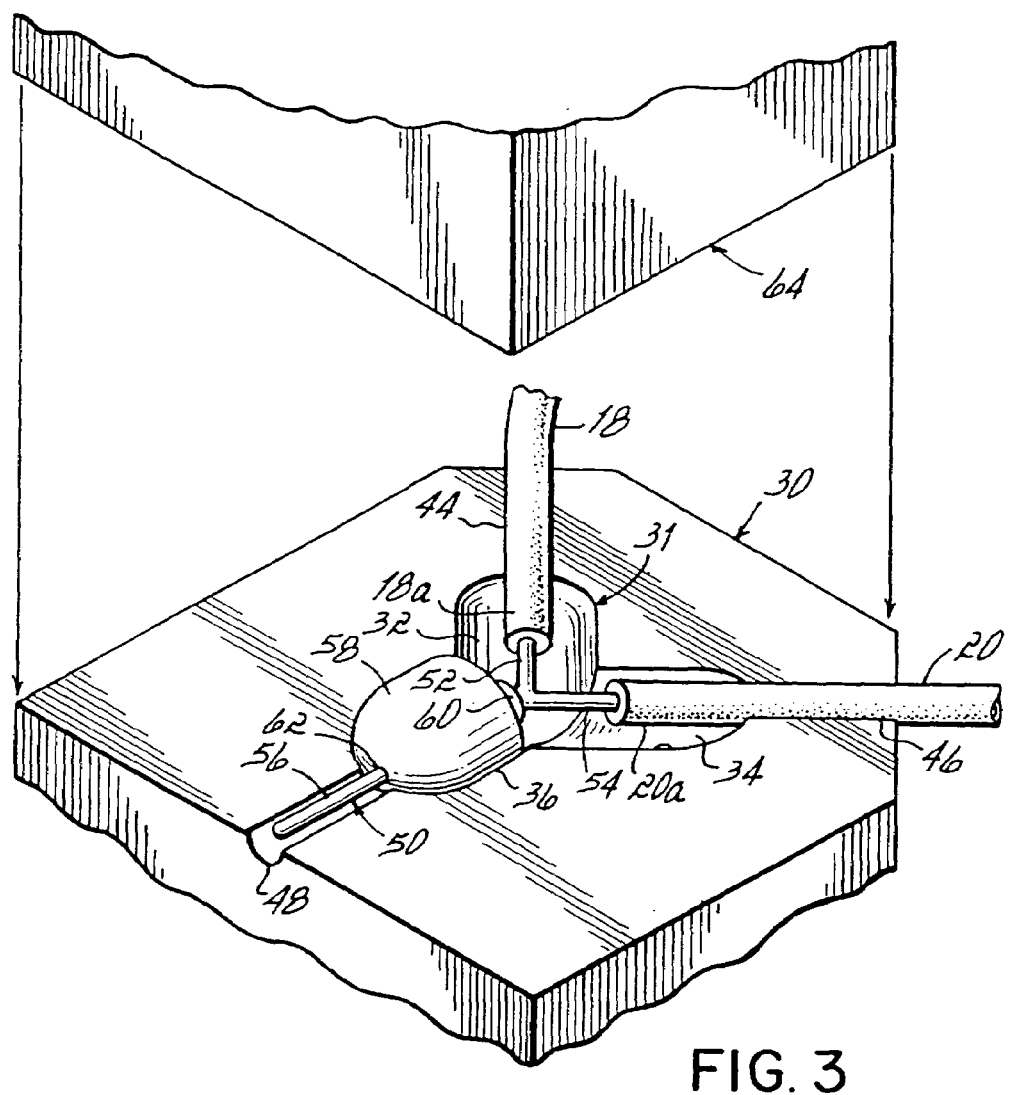
FIG. 3 is a perspective view of the molding process at a later stage.
Figure 4:
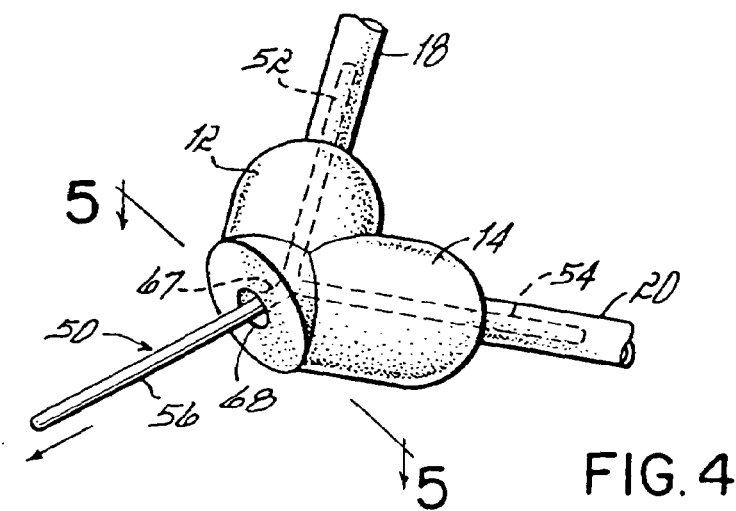
FIG. 4 is a perspective view of an intermediate product formed by the molding process.

The items described with respect to FIG. 2 are attached together and placed within mold half 30 as shown in FIG. 3 and a second mold half 64 is brought into facing engagement with mold half 30. It will be understood that mold half 64 has cavities and recesses (not shown) which are the mirror image of cavity portions 32, 34, 36 and recesses 44, 46, 48 of mold half 30. The mold is then shot, i.e., curable mold material is injected into cavities 32, 34 of mold 30 through ports 38, 40, and after curing thereof, an intermediate product as shown in FIG. 4 will result. In this step, cavities 32, 34 act as one cavity for producing connector portions 12, 14 which, in turn, form a single integral connector portion. Metal mold insert 58 is removed from rod member 56 and then the "Y" shaped inner mold member 50 is withdrawn from connector portions 12, 14 and tubes 18, 20 by pulling on rod member 56. Mold member 50 is flexible and may be withdrawn with reasonable manual force being applied by a pair of pliers.

Figure 5:
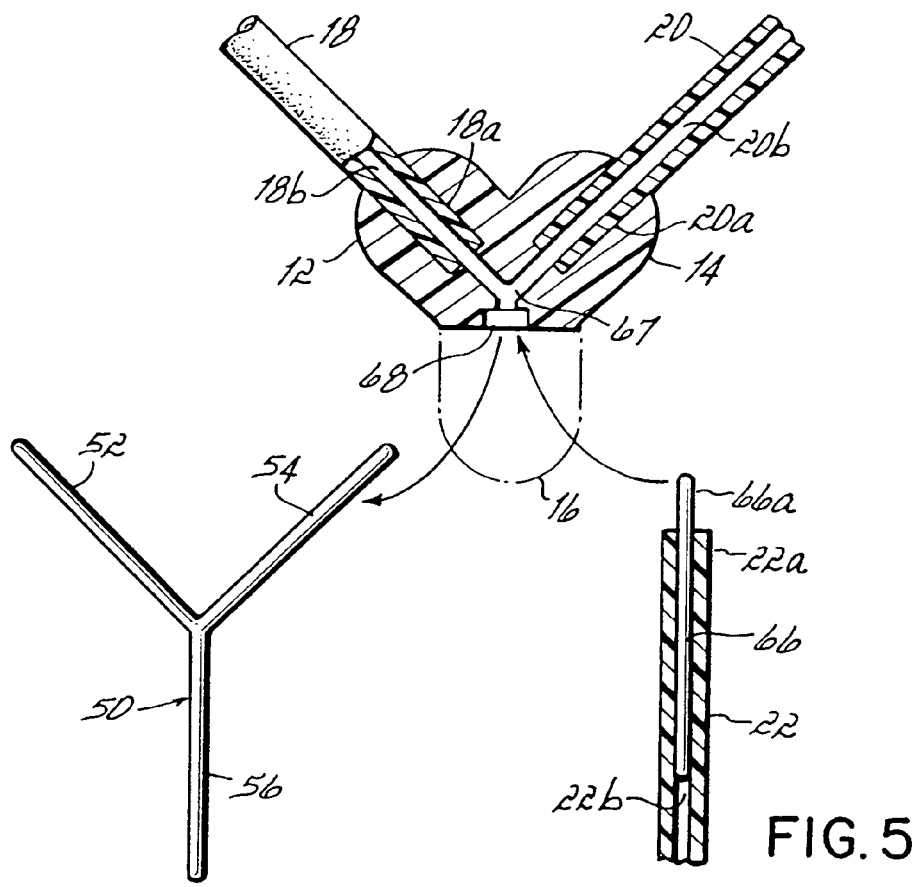
FIG. 5 is a sectional view taken generally along line 5—5 of FIG. 4 and also showing the removal of an internal "Y" shaped mold member as well as an additional tube containing a rod used later in the molding process; and, FIG. 6 is the intermediate product shown in perspective within the mold cavity with the third tube in place just prior to the final molding step.
Figure 6:
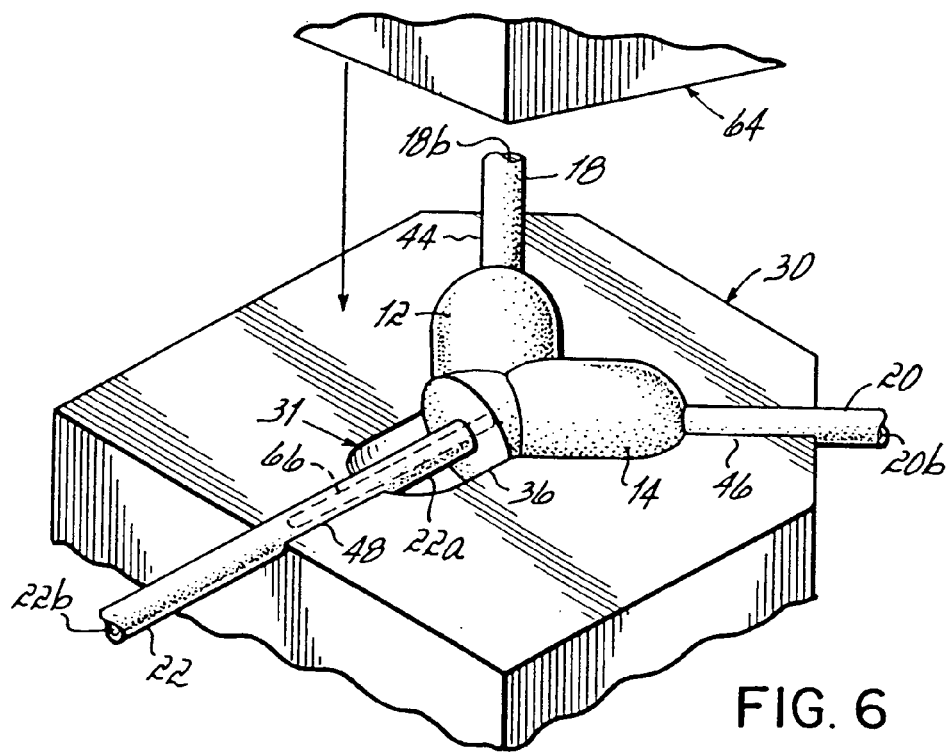

After mold member 50 is withdrawn, as shown in FIG. 5, the third tube 22 is prepared for the final molding step. That is, a straight plastic rod 66, also preferably formed of LDPE, is inserted into tube end 22a with a small portion 66a extending outwardly from end 22a. This assembly is placed into mold half 30 as shown in FIG. 6 with rod end 66a extending into a passage 67 formed within connector portions 12, 14 by rod member 56 and with tube end 22a held within a recess 68 formed by protrusion 60 (FIG. 2) on mold insert 58. It will therefore be appreciated that rod end 66a will maintain fluid passage 67 open during the second molding step. Mold half 64 is again brought into facing engagement with mold half 30 and the final cavity 36 is injected with curable mold material, again taking the form of conventional liquid silicone. After this portion of connector 11 has cured, rod 66 may be blown out of tube 22 by injecting pressurized air into tube 18 after tube 20 has been plugged, or into tube 20 after tube 18 has been plugged.

Although a preferred embodiment of the present invention has been shown and described, along with a preferred method of making the product of this invention, the details provided herein are not intended to limit the scope of protection. For example, certain modifications such as the incorporation of additional connector portions and tubes are possible as well as the use of any number of shapes for the connector. The connector portions do not have to have readily distinguishable shapes as specifically preferred herein, but may be formed as part of one shape. It will also be appreciated that multiple connectors of this invention may be used in a single system. Those of ordinary skill will readily recognize many further modifications within the spirit and scope of the inventive concepts. Therefore, Applicants intend to be bound only by the legal scope of the appended claims.

What is claimed is:

1. A mold and tubing assembly comprising:
   at least three silicone, hollow, flexible tubes each including a free end;
   a mold having first and second mold portions engaged to form a substantially closed cavity and supporting at least a portion of the three free ends within the mold;
   a passage forming assembly including rod portions disposed within the free ends of each of the three tubes; and
   curable liquid silicone disposed in the cavity about the portions of the three ends and at least a portion of the passage forming assembly, wherein the passage forming assembly is configured to form a generally smooth passage between the three tubes after the liquid silicone is cured and the rod portion is removed.

2. The assembly of claim 1, wherein the rod portions include at least first, second and third rod members.

3. The assembly of claim 1, wherein the rod portions form a "Y" shaped assembly.

4. The assembly of claim 3, wherein the "Y"-shaped assembly is a single-piece.

5. The assembly of claim 3, wherein the rod portions include (i) first and second rod portions forming the Y-shaped assembly, and further include (ii) a third rod portion comprising a straight rod.

6. The assembly of claim 1, wherein the passage forming assembly is non-silicone.

7. The assembly of claim 1, wherein the passage forming assembly is metallic.

8. The assembly of claim 7, wherein the passage forming assembly is stainless steel.

9. The assembly of claim 1, wherein at least one of the mold portions includes at least one port.

10. A mold and tubing assembly comprising:
    at least three silicone, flexible tubes each including a free end with an interior surface having respective interior diameters;
    a mold having first and second mold portions engaged to form a substantially closed cavity and supporting at least a portion of the three free ends within the mold;

a passage forming assembly including at least three rod members, with a portion of each of the rod members being disposed within a respective free end of the three tubes; and liquid silicone disposed in the cavity about the portions of the three ends and at least a portion of the passage forming assembly.

11. The assembly of claim 10, wherein the passage forming assembly is configured to form a generally smooth passage between the three tubes after the liquid silicone is cured and the passage forming assembly is removed.

12. The assembly of claim 11, wherein at least one of the mold portions includes at least one port.

13. The assembly of claim 11, wherein the rod members form a "Y"-shaped assembly.

14. The assembly of claim 13, wherein the "Y"-shaped assembly is a single-piece.

15. The assembly of claim 13, wherein the rod members include (i) first and second rod members forming the Y-shaped assembly, and further include (ii) a third rod member comprising a straight rod.

16. The assembly of claim 11, wherein the rod members are non-silicone.

17. The assembly of claim 11, wherein the rod members are metallic.

18. The assembly of claim 17, wherein the rod members are stainless steel.

* * * * *